United States Patent
Lee et al.

(10) Patent No.: US 8,392,136 B2
(45) Date of Patent: Mar. 5, 2013

(54) IN-PLACE MANAGEMENT OF SEMICONDUCTOR EQUIPMENT RECIPES

(75) Inventors: Chris W. Lee, Fremont, CA (US); Dominic G. David, Chennai (IN)

(73) Assignee: KLA-Tencor Corporation, Milpitas, CA (US)

( * ) Notice: Subject to any disclaimer, the term of this patent is extended or adjusted under 35 U.S.C. 154(b) by 297 days.

(21) Appl. No.: 12/833,350

(22) Filed: Jul. 9, 2010

(65) Prior Publication Data

US 2012/0010843 A1  Jan. 12, 2012

(51) Int. Cl.
G06F 19/00 (2011.01)
G01N 21/00 (2006.01)

(52) U.S. Cl. ........................... 702/83; 356/237.1

(58) Field of Classification Search .................... 702/83; 356/237.1; 250/492.1
See application file for complete search history.

(56) References Cited

U.S. PATENT DOCUMENTS

| | | | |
|---|---|---|---|
| 5,760,893 A * | 6/1998 | Raymond | 356/237.1 |
| 7,601,240 B2 | 10/2009 | Kagoshima et al. | |
| 7,987,072 B2 * | 7/2011 | Teshima et al. | 702/183 |
| 2004/0021856 A1 | 2/2004 | Nishiyama | |
| 2007/0053581 A1 | 3/2007 | Ueno et al. | |
| 2009/0228217 A1 | 9/2009 | Fukushima | |

* cited by examiner

Primary Examiner — Bryan Bui
(74) Attorney, Agent, or Firm — Suiter Swantz pc llo

(57) ABSTRACT

Systems and methods for managing optical inspection target components are disclosed. A method may include, but is not limited to: storing at least one external recipe component at an inspection tool node; associating at least one proxy component with the at least one external recipe component; associating the at least one external recipe component with at least one optical inspection target recipe; and storing the at least one optical inspection target recipe including the at least one proxy component in a recipe distribution server. A method may include, but is not limited to: receiving a selection of at least one recipe associated with an optical inspection target to be inspected at a first inspection tool node; and determining whether one or more external recipe components associated with the recipe are stored on at least one of the first inspection tool node and a second node.

16 Claims, 10 Drawing Sheets

IN-PLACE MANAGEMENT OF SEMICONDUCTOR EQUIPMENT RECIPES

BACKGROUND

In optical defect inspection (e.g. semiconductor verification processes), systems may include databases containing information regarding design specification of various structural components (e.g. threshold distances between registration marks) of an optical inspection target (e.g. a semiconductor device). For a particular optical inspection target, the system may maintain recipe data reflecting a combination of multiple structural components selected from the component database that are incorporated to create the optical inspection target. The recipe may include all the information required to perform an inspection or to classify defects relating to the optical inspection target.

For example, in order to increase the quality of inspection, high-resolution image data associated with a proper optical target design may be maintained so that data may be compared to inspection data associated with an optical target under test. Each optical target structure may have multiple images associated therewith. As such, the quantity of data involved in such inspection processes may be immense.

In the case of distributed optical defect inspection systems including multiple inspection tools accessing a single component library, the data transfer overhead associated with the movement of such large files may become prohibitive. As such, it may be desirable to provide a recipe distribution system (RDS) for the transfer and management of optical inspection target recipes.

SUMMARY

Systems and methods for managing optical inspection target components are disclosed.

A method may include, but is not limited to: storing at least one external recipe component at an inspection tool node; associating at least one proxy component with the at least one external recipe component; associating the at least one external recipe component with at least one optical inspection target recipe; and storing the at least one optical inspection target recipe including the at least one proxy component in a recipe distribution server.

A method may include, but is not limited to: receiving a selection of at least one recipe associated with an optical inspection target to be inspected at a first inspection tool node; and determining whether one or more external recipe components associated with the recipe are stored on at least one of the first inspection tool node and a second node.

A system may include, but is not limited to: a first optical inspection node including a datastore maintaining a first external recipe component; a second optical inspection node including a datastore maintaining a second external recipe component; and a recipe distribution server including a datastore maintaining at least one optical inspection target recipe associated with the first external recipe component and the second external recipe component.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

In the following detailed description of exemplary embodiments, reference is made to the accompanying drawings, which form a part hereof. In the several figures, like referenced numerals identify like elements. The detailed description and the drawings illustrate exemplary embodiments. Other embodiments may be utilized, and other changes may be made, without departing from the spirit or scope of the subject matter presented here. The following detailed description is therefore not to be taken in a limiting sense, and the scope of the claimed subject matter is defined by the appended claims.

In order to minimize the transfer of large optical target component data files, such files may be maintained in datastores external to a central processing unit and transferred in an on-demand manner across a peer-to-peer network at the direction of the central processing unit.

Reference will now be made in detail to the subject matter disclosed, which is illustrated in the accompanying drawings.

Figure 1:
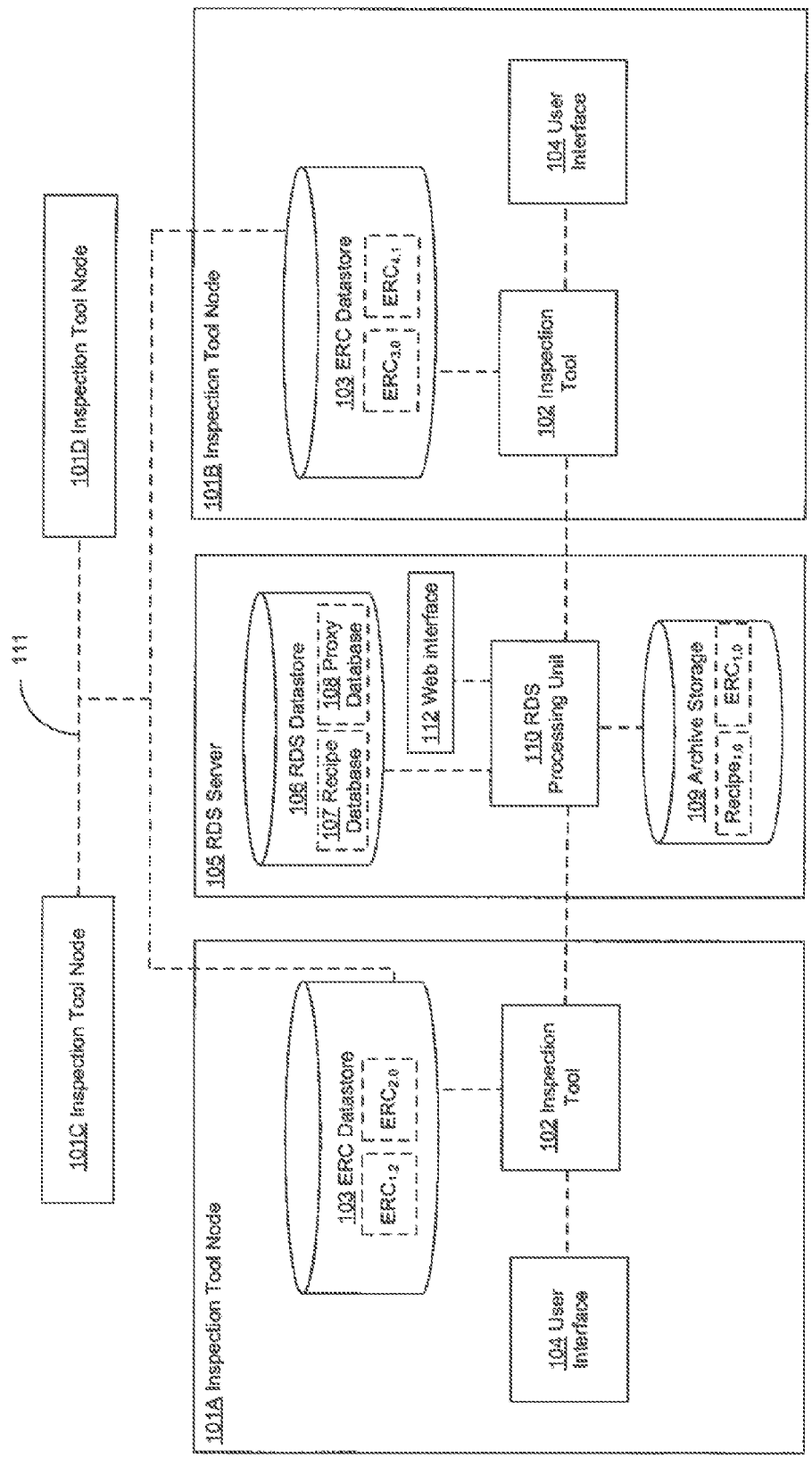
FIG. 1 shows a system for storage and distribution of external recipe components.

Referring to FIG. 1, an optical inspection target recipe distribution system (RDS) 100 is shown. The RDS 100 may include at least an inspection tool node 101A, an inspection tool node 101B, an inspection tool node 101C and an inspection tool node 101D. It will be recognized that the present descriptions may be extended to any number of inspection tool nodes 101 through the addition or removal of inspection tool nodes. An inspection tool node 101 may include at least one inspection tool 102 (e.g. a scatterometry device, brightfield microscope, darkfield microscope, electron beam device and the like). The inspection tool node 101 may be configured to carry out various inspection operations (e.g. patterned or bare wafer micro-defect inspection, patterned or bare wafer macro-defect inspection, reticle defect inspection, high-resolution wafer review, film thickness measurement, solar cell defect inspection, LED defect inspection, and the like).

An inspection tool node 101 may utilize recipes to carry out inspection of various target structures (e.g. semi-conductor wafer samples). A recipe may define the setup parameters for particular operations associated with a particular target and/or inspection tool 102. A host system may transmit a command to an inspection tool node 101 to carry out an inspection utilizing a particular recipe. The recipe may define various setup parameters (e.g. inspection tool 102 parameters, process setup parameters, optics parameters, sensitivity settings, image processing algorithm parameters, result analysis settings and the like). The inspection tool node 101 may request the most recent version of the recipe from the RDS 100 and the recipe may be provided to the inspection tool node 101 (as discussed in detail below). Upon receipt of a given recipe, the inspection tool node 101 may parse the recipe to obtain the setup parameters associated with the desired inspection operations and load those parameters into an inspection tool 102. Following setup, the inspection tool 102 may perform initialization and run routines according to the supplied recipe parameters to carry out inspection operations according to the recipe parameters. Alignment, detection and other algorithms will use the parameters as inputs in order to perform their tasks during the inspection process.

The inspection tool node 101A and the inspection tool node 101B may include an external recipe component (ERC) datastore 103. An ERC datastore 103 may store data regarding various structural components of an optical target. An ERC datastore 103 may contain ERC data for a variety of structural components (e.g. $ERC_{1\_x}$, $ERC_{2\_x}$, $ERC_{3\_x}$, $ERC_{4\_x}$) as well as recipe data detailing the combinations of those structural components which form an optical target (e.g. $Recipe_{1\_x}$, $Recipe_{2\_x}$). ERC data may include multiple wafer swath images. The size of these ERCs may range from a few GB to a few TB depending on the total wafer area recorded and the recording pixel size. An inspection tool node may further include an interface 104 configured to receive manual (e.g. from a human user) or automated (e.g. from a control system) input to direct the inspection of various optical targets.

Figure 2:
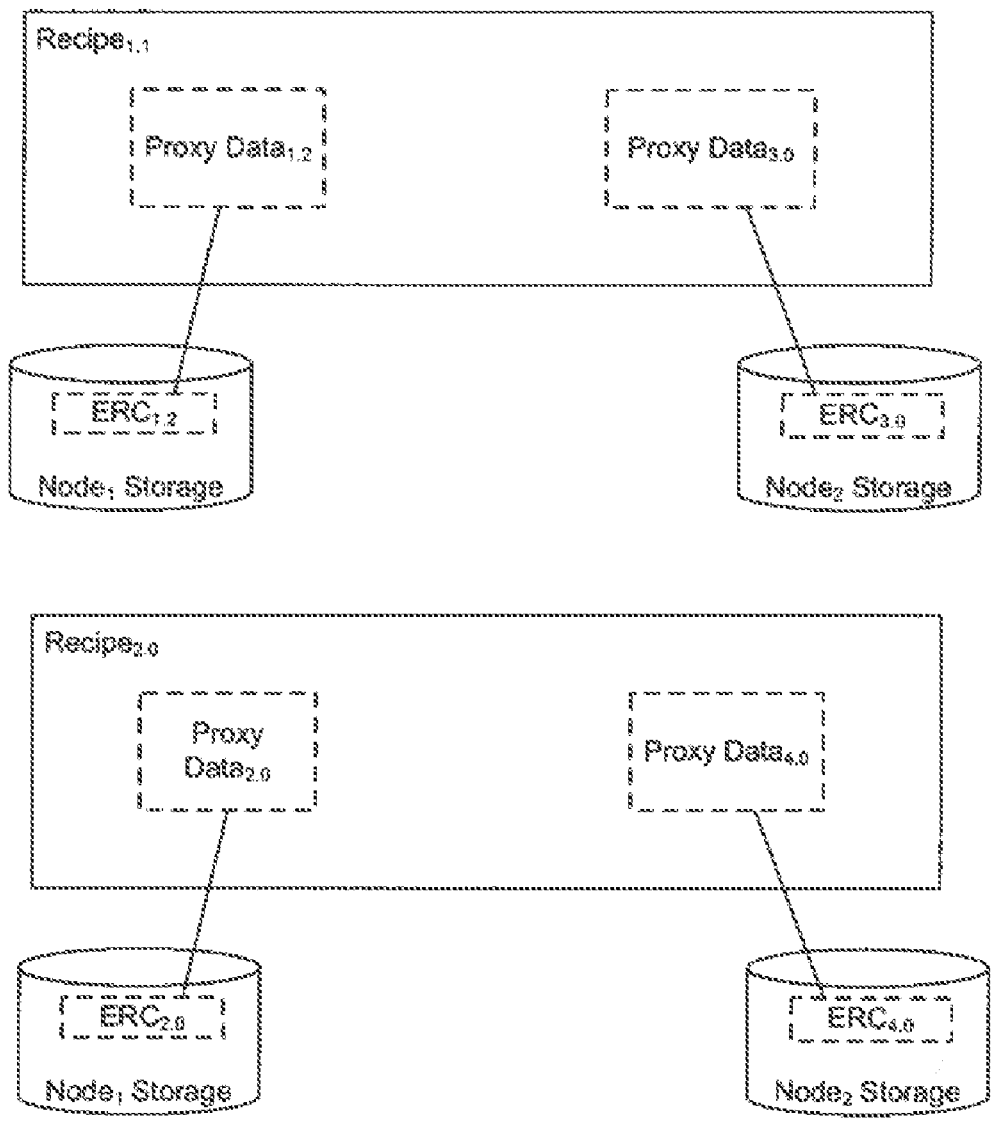
FIG. 2 shows mappings between proxy components of an optical inspection target recipes and associated external recipe component storage locations.

It may be the case that an ERC cannot be saved into a central server database due to the volume of data contained in the ERC. Instead, a smaller proxy component that references the large data may be incorporated. This proxy component may include an XML file that contains meta-data describing the ERC. Recipes associated with a particular ERC may contain a reference to the proxy. Referring to FIG. 2, an optical target recipe (e.g. $Recipe_{1.2}$) may include references to smaller proxy components (e.g. $Proxy_{1.2}$, $Proxy_{3.0}$). For example, each proxy component may provide a mapping to a particular larger ERC. For example, $Recipe_{1.2}$ may utilize two optical target components $ERC_{1\_x}$ and $ERC_{3\_x}$. It may be the case that a required version of $ERC_{1\_x}$ and $ERC_{3\_x}$ (e.g. $ERC_{1.2}$ and $ERC_{3.0}$) are maintained on storage associated with distinct inspection tool nodes 101 (e.g. inspection tool node 101A and inspection tool node 101B).

Proxy components (e.g. $Proxy_{1.2}$) may include a distinct identifier that maps to the storage location of its associated ERC (e.g. $ERC_{1.2}$). For example, each version of recipe and the ERCs associated therewith, the RDS 100 may maintain a global unique identifier (GUID) (e.g. $GUID_1$, $GUID_2$ and $GUID_3$) uniquely assigned to a particular version of an ERC (e.g. $ERC_{1.0}$, $ERC_{1.1}$, $ERC_{1.2}$). Similarly, GUIDs (e.g. $GUID_4$, $GUID_5$ and $GUID_5$) may be uniquely assigned to particular versions of recipes (e.g. $Recipe_{1.0}$, $Recipe_{1.1}$ and $Recipe_{1.2}$).

In the case where an inspection tool seeks to utilize a recipe requiring one or more ERCs that are not contained in its local datastore, it may be necessary to provide those ERCs to that inspection tool. Referring again to FIG. 1, to facilitate the transfer of ERCs between inspection tool nodes 101, the RDS 100 may include an RDS server 105 configured to manage the distribution of recipes and ERCs between the inspection tool nodes 101 by monitoring the locations of various ERCs by maintaining a database of recipes and the proxy components associated with the ERCs of those recipes.

Figure 3:
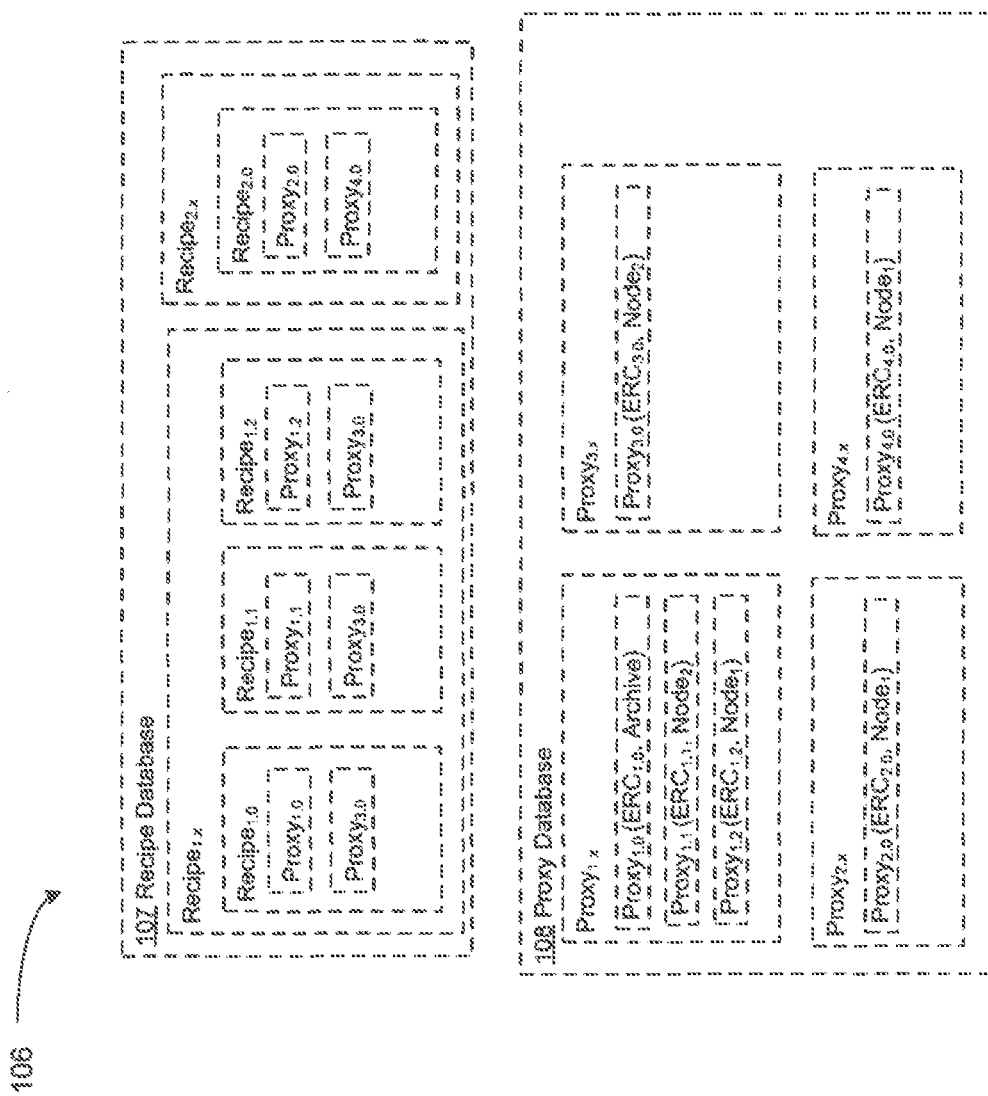
FIG. 3 shows a recipe distribution system database.

Referring to FIGS. 1 and 3, the RDS server 105 may include an RDS datastore 106 for storage of copies of recipes used by the inspection tool nodes 101 as well as the underlying proxy components linking to the ERCs employed by those recipes. The RDS datastore 106 may include a recipe database (e.g. recipe database 107) containing copies of various versions of a recipe (e.g. $Recipe_{1\_x}$, $Recipe_{2\_x}$). Each version of a recipe (e.g. versions $Recipe_{1.0}$, $Recipe_{1.1}$ and $Recipe_{1.2}$ of $Recipe_{1\_x}$) may maintain references to the versions of the proxies that they employ (e.g. $Recipe_{1.2}$ uses $Proxy_{1.2}$ (i.e. the proxy associated with a third version of an $ERC_{1\_x}$) and $Proxy_{2.0}$ (i.e. the proxy associated with a first version of an $ERC_{2\_x}$). Further, the RDS datastore 106 may include a proxy database 108 containing copies of each proxy associated with a version of an ERC. For example the proxy database 108 may maintain various versions a $Proxy_{1\_x}$ (e.g. $Proxy_{1.0}$ associated with a first version of $ERC_{1\_x}$ stored at an archive storage 109, $Proxy_{1.1}$ associated with a second version of $ERC_{1\_x}$ stored at inspection tool node 101B and $Proxy_{1.2}$ associated with a third version of $ERC_{1\_x}$ stored at inspection tool node 101A).

Such awareness by the RDS 100 of the locations of the various ERCs may allow the RDS 100 to manage the transfer of ERCs between inspection tool nodes 101 where the ERCs are required for setup, run and review operations associated with optical target inspection.

Referring to FIGS. 4-10, a series of illustrations depicting implementations of processes are shown. For ease of understanding, certain illustrations are organized such that the initial illustrations present implementations via an overall viewpoint and thereafter the following illustrations present alternate implementations and/or expansions of the initial illustrations as either sub-steps or additional steps building on one or more earlier-presented illustrations. This style of presentation utilized herein (e.g., beginning with a presentation of a illustration(s) presenting an overall view and thereafter providing additions to and/or further details in subsequent illustrations) generally allows for a rapid and easy understanding of the various process implementations.

Figure 4:
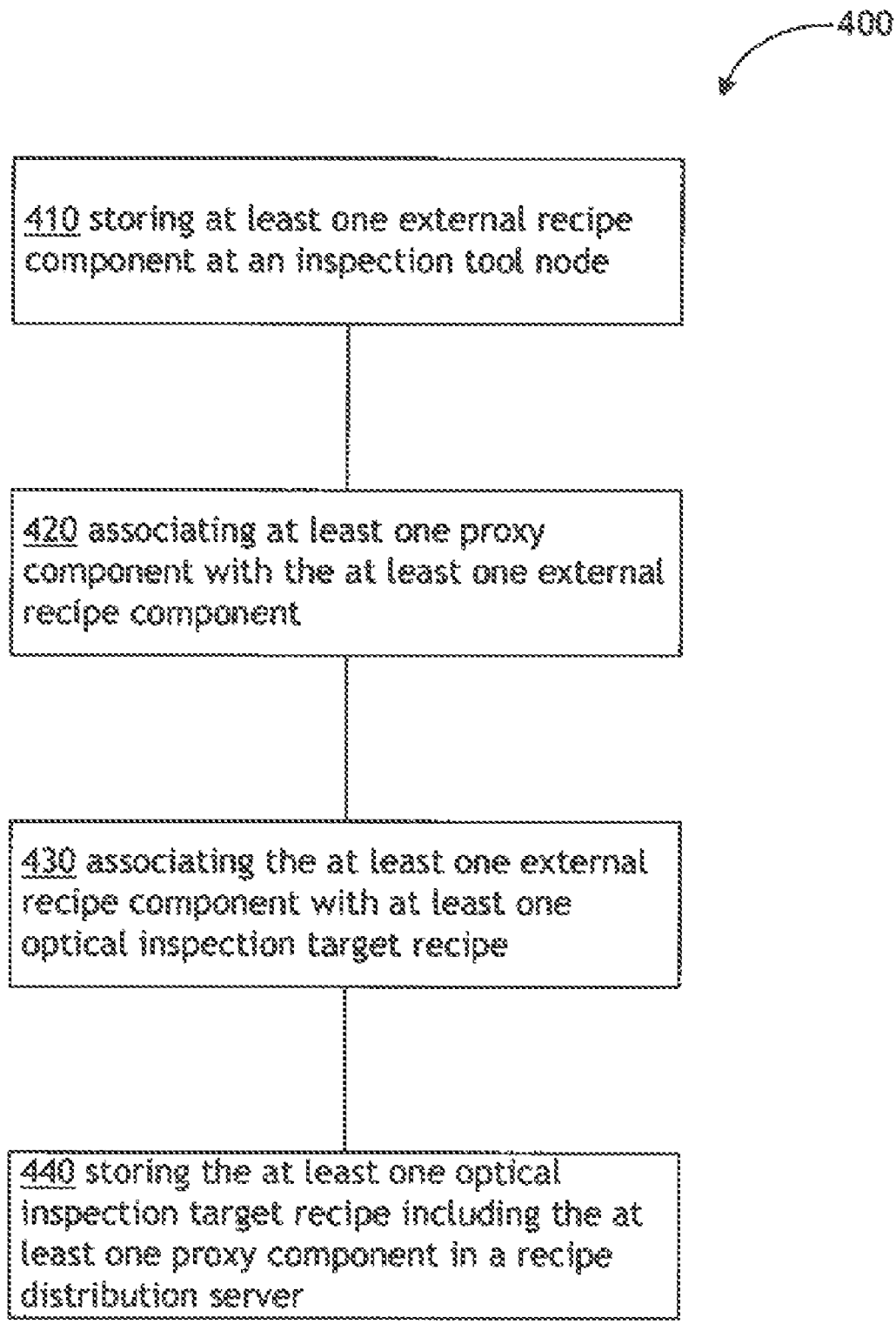
FIG. 4 shows a process for managing distributed external recipe components.

In FIG. 4 and in following figures representing various exemplary methods for distribution and management of ERCs between inspection tool nodes 101. The operational flows, discussion and explanation may be provided with respect to the above-described examples of FIGS. 1-3, and/or with respect to other examples and contexts. However, it should be understood that the operational flows may be executed in a number of other environments and contexts, and/or in modified versions of FIGS. 1-3. In addition, although the various operational flows are presented in the sequence(s) illustrated, it should be understood that the various operations may be performed in orders and combinations than those that are illustrated. For example, any operational step may be combined with any other operational step in any order.

In order to establish a network of distributed recipes and their associated ERCs, the RDS 100 may carry various management operations.

Referring to FIG. 4, a method 400 for external recipe component management is illustrated. Operation 410 depicts storing at least one external recipe component at an inspection tool node. As shown in FIGS. 1-3, an interface (e.g. interface 104) may be accessed by user (e.g. a human user or a peripheral system) in order to define the parameters of an ERC (e.g. inspection device parameters, process setup parameters, optics parameters, sensitivity settings, image processing algorithm parameters, result analysis settings and the like) and/or associate one or more data records (e.g. wafer swath images from an imaging device, ERC IDs, ERC version IDs, metadata, checksums, storage location references, modification date/time stamps, recipe size and the like) with an ERC. The ERC may be saved to the ERC datastore 103 of an inspection tool node 101B as a newly created $ERC_{1.0}$.

Operation 420 depicts associating at least one proxy component with the at least one external recipe component. For example, as shown in FIGS. 1-3, it may be the case that an ERC files cannot be saved into a central server database due to the volume of data contained in the ERC. In such a case, a proxy component element (e.g. $Proxy_{1.2}$ and $Proxy_{3.0}$) may be associated with a storage location of a corresponding ERC (e.g. $ERC_{1.2}$ and $ERC_{3.0}$). For example, an inspection tool node (e.g. inspection tool node 101A) may create a proxy component file containing meta-data referencing a storage location (e.g. a network address) of a particular ERC as well as other characteristics of the ERC (e.g. a checksum value).

Operation 430 depicts associating the at least one external recipe component with at least one optical inspection target recipe. Following the creation of an ERC, the ERC may be associated with one or more optical inspection target recipes. For example, as shown in FIGS. 1-3, an interface (e.g. interface 104) may be accessed by user (e.g. a human user or a peripheral system) to define a recipe (e.g. $Recipe_{1.1}$) which combines various component structures defined by one or more ERCs (e.g. $ERC_{1.1}$ and $ERC_{3.0}$).

Operation 440 depicts storing the at least one optical inspection target recipe including the at least one proxy component in a recipe distribution server. For example, as shown in FIGS. 1-3, following the association of one or more proxy component with their corresponding ERCs, a recipe associated with those ERC may be provided to a centralized recipe server. For example, a recipe defined at the inspection tool node 101A and including the proxy component associated with any required ERCs may be transmitted to the RDS server 105 for storage in the recipe database 107 of the ERC datastore 103.

Figure 5:
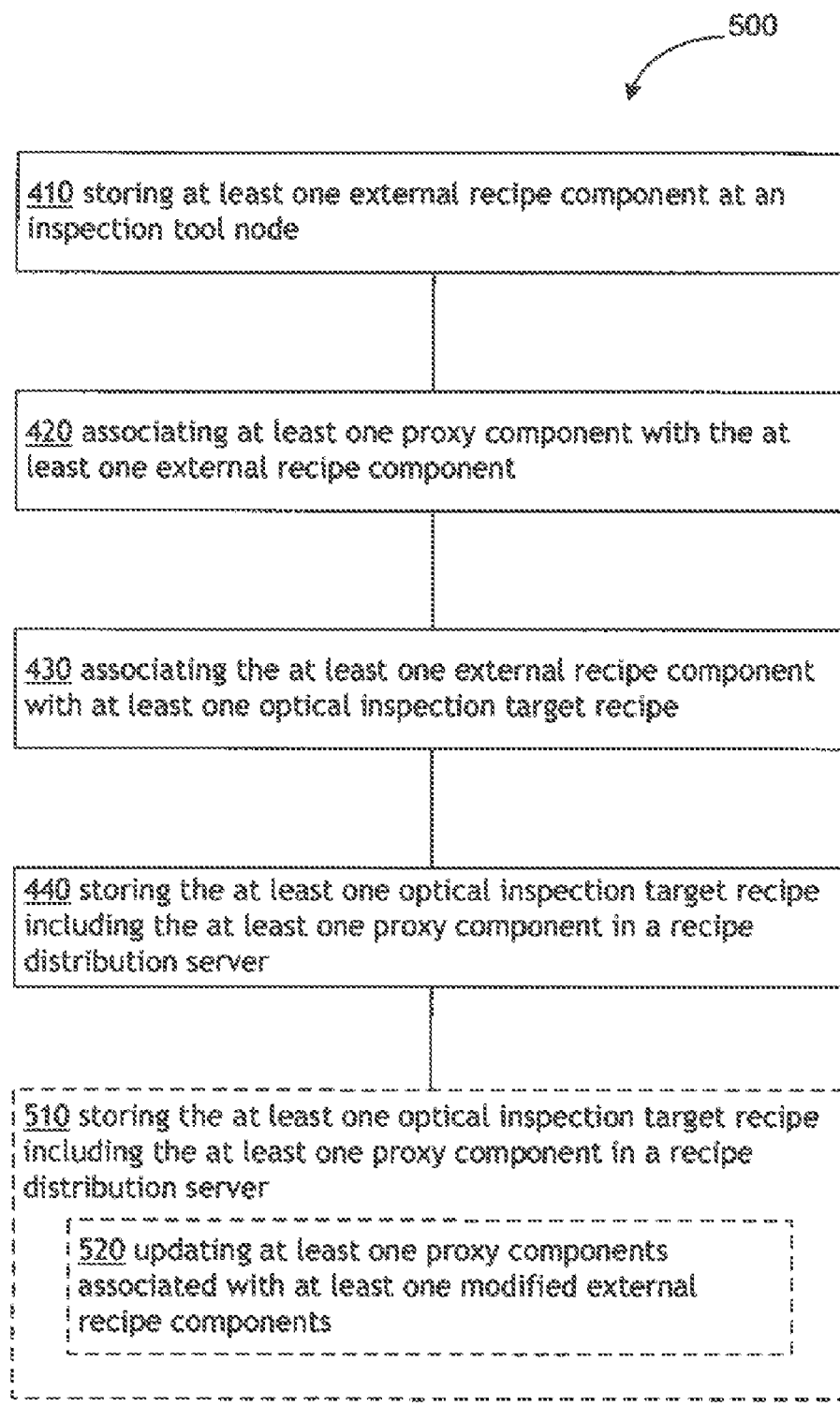
FIG. 5 shows a process for managing distributed external recipe components.

Referring to FIG. 5, the method 400 of FIG. 4 may include one or more additional operations. The method 400 may include an operation 510 and/or an operation 520.

Operation 510 depicts modifying at least one external recipe components. For example, as shown in FIGS. 1-3, a user (e.g. a human user or a peripheral device) may access interface 104 of inspection tool node 101B and load $ERC_{1.0}$ from ERC datastore 103. The characteristics of the $ERC_{1.0}$ may be modified and a new version of the ERC (e.g. $ERC_{1.1}$) may be saved to the ERC datastore 103 of the inspection tool node 101B.

Operation 520 depicts updating at least one proxy components associated with at least one modified external recipe components. For example, as shown in FIGS. 1-3, following a modification of an ERC (e.g. $ERC_{1.0}$ is modified to $ERC_{1.1}$ by inspection tool node 101B), the proxy component associated with that ERC may be updated to correspond to the modified ERC (e.g. $Proxy_{1.1}$ may be created referencing new version $ERC_{1.1}$). The updated proxy component may be provided to the RDS server 105 where an updated version of one or more recipes utilizing $ERC_{1.x}$ (e.g. $Recipe_{1.1}$) may be created including new proxy component (e.g. $Proxy_{1.1}$) referring to updated ERC (e.g. $ERC_{1.1}$). The updated proxy component may be incorporated into all recipes utilizing $ERC_{1.x}$ or a subset thereof.

Each ERC version (e.g. $ERC_{1.x}$), recipe version (e.g. $Recipet_{1.x}$) or proxy component version (e.g. $Proxy_{1.x}$) may include a GUID to uniquely identify each element being saved in the RDS 100. Also, each ERC version (e.g. $ERC_{1.x}$), recipe version (e.g. $Recipe_{1.x}$) or proxy component version (e.g. $Proxy_{1.x}$) may include a checksum mechanism to verify the propriety of an ERC being saved to the RDS 100 to determine if the ERC has been corrupted. Once the RDS 100 has located a particular ERC, recipe or proxy component according to its GUID, the RDS 100 may employ the checksum to determine if the ERC, recipe or proxy component has changed. This may enable the avoidance of duplicate versions and allow for the identification of identical components present on different tools/data stores.

Figure 6:
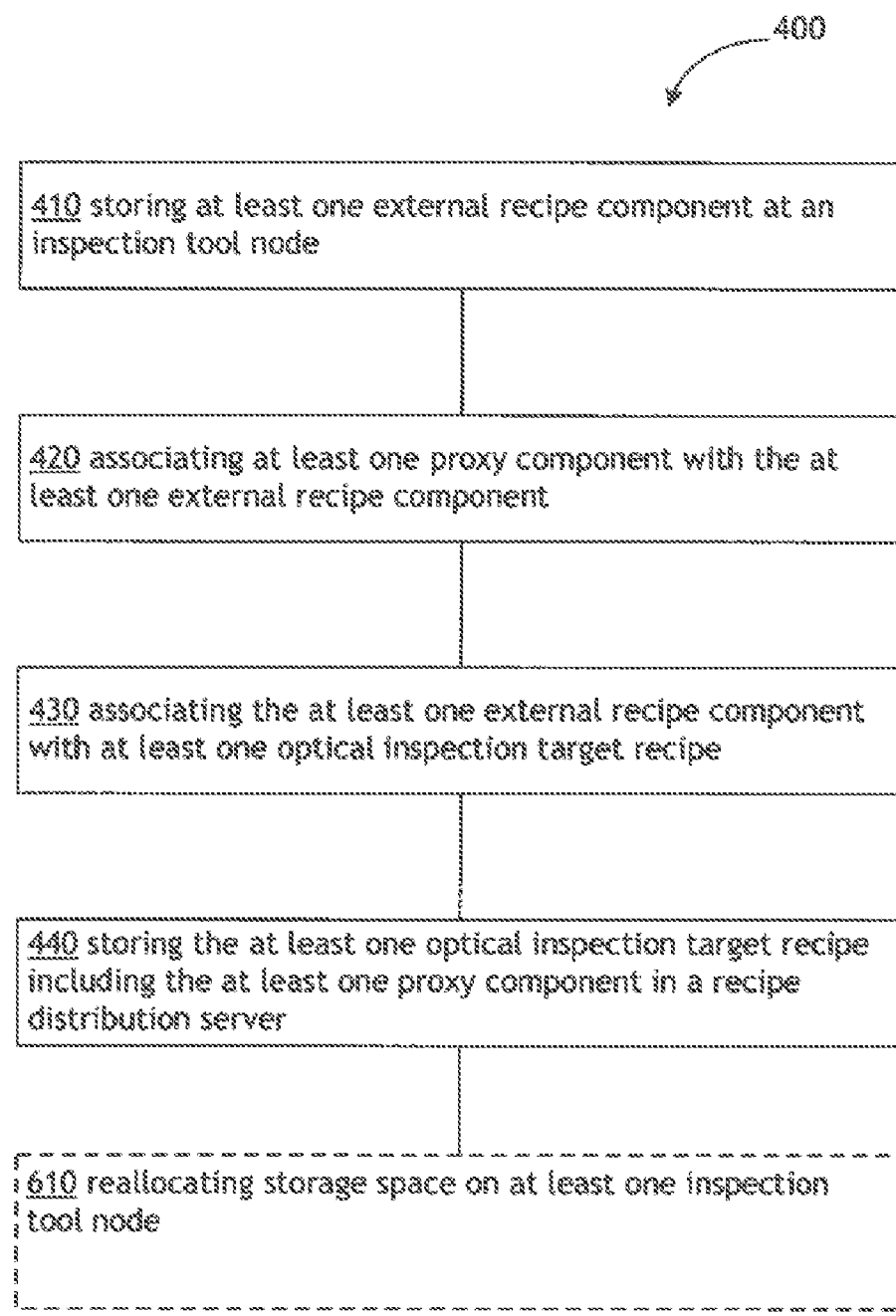
FIG. 6 shows a process for managing distributed external recipe components.

Referring to FIG. 6, the method 400 of FIG. 4 may include one or more additional operations. The method 400 may include an operation 610.

Operation 610 depicts reallocating storage space on at least one inspection tool node. For example, as shown in FIGS. 1-3, following the creation of multiple ERCs and/or modifications to those ERCs resulting in newly created versions of the ERCs, it may be the case that an ERC datastore 103 associated with an inspection tool node 101 may reach its storage capacity. At this point, the RDS 100 may reallocate storage space associated with certain ERCs (e.g. delete or archive). To facilitate such operations, the RDS 100 may track ERC usage. The RDS 100 may track storage metrics for an ERC including: least used ERC, last used timestamp, list of recipes linking to a given ERC, orphaned ERCs and/or the number of copies of a single version of an ERC. The RDS 100 may provide notifications to a user (e.g. via interface 104, an RDS server dashboard and/or email notification) when an ERC datastore 103 nears its capacity.

At this point, ERCs for an ERC datastore 103 associated with a particular inspection tool node 101 may be manually deleted or archived to archive storage 109 associated with the RDS server 105 by a user. Alternately, the RDS server 105 may be configured to execute ERCs maintenance rules to automatically archive and purge ERCs when required according to various storage metrics associated with the ERCs. In this way, the storage space may be regulated across the RDS 100 rather than with respect to an individual inspection tool node 101. If an ERC datastore 103 for an inspection tool node 101A is nearly full, the inspection tool node 101A may query the RDS server 105 to determine whether or not a particular ERC version may be deleted from the ERC datastore 103. The RDS server 105 may analyze the recipes and associated proxy components of the RDS datastore 106 to establish a priority for deletion/archiving of ERCs. For example, an ERC for which multiple copies exist in the RDS 100 (e.g. redundant) may be assigned a higher delete/archive priority than an ERC for which only one copy exists in the RDS 100. Similarly, an ERC that is not referenced by any recipes (e.g. an orphan) currently in use by an inspection tool node may be assigned a higher delete/archive priority. When additional storage space is required at an inspection tool node 101, the RDS server 105 may automatically delete/archive one or more ERCs according to its priority or provide the priority information to the inspection tool node 101 to facilitate delete/archive determinations by a user.

Following archiving, the RDS server 105 may maintain the association between a recipe (e.g. $Recipe_{1.0}$) and/or an associated ERC (e.g. $ERC_{1.0}$) even if the recipe and/or the ERC has been previously archived so as to facilitate restoration of the recipe and/or ERC to an inspection tool node 101 in the future.

The RDS server 105 may provide additional functionality facilitating ERC management. For example, the RDS server 105 may provide a list of all ERCs present on the RDS 100.

The list may be sorted by inspection tool node (e.g. which ERCs are present on a particular node), ERC (e.g. which recipes are linking to a particular ERC, how many copies of this ERC are present on this network, which inspection tool node contain copies of this ERC) or by each recipe (e.g. the number of ERCs is a recipe linked to, inspection tool nodes 101 contain copies of the recipe). Further, the RDS server 105 may provide meta-data information regarding an ERC (e.g. recipe parameters used to validate the contents of the ERC, ERC usage information, recipes linked to the ERC, locations of the ERC on the RDS 100, and/or a list of ERCs linked to a subject ERC). Still further, the RDS server 105 may communicate in a scheduled or on-demand manner with a inspection tool node 101 in order to synchronize the proxy component and recipe data maintained in the RDS datastore 106 with the current status of the ERC datastore 103 of the inspection tool node 101.

In the case where an inspection tool seeks to utilize a recipe requiring one or more ERCs that are not contained in its local datastore, it may be necessary to distribute those ERCs to that inspection tool.

Figure 7:
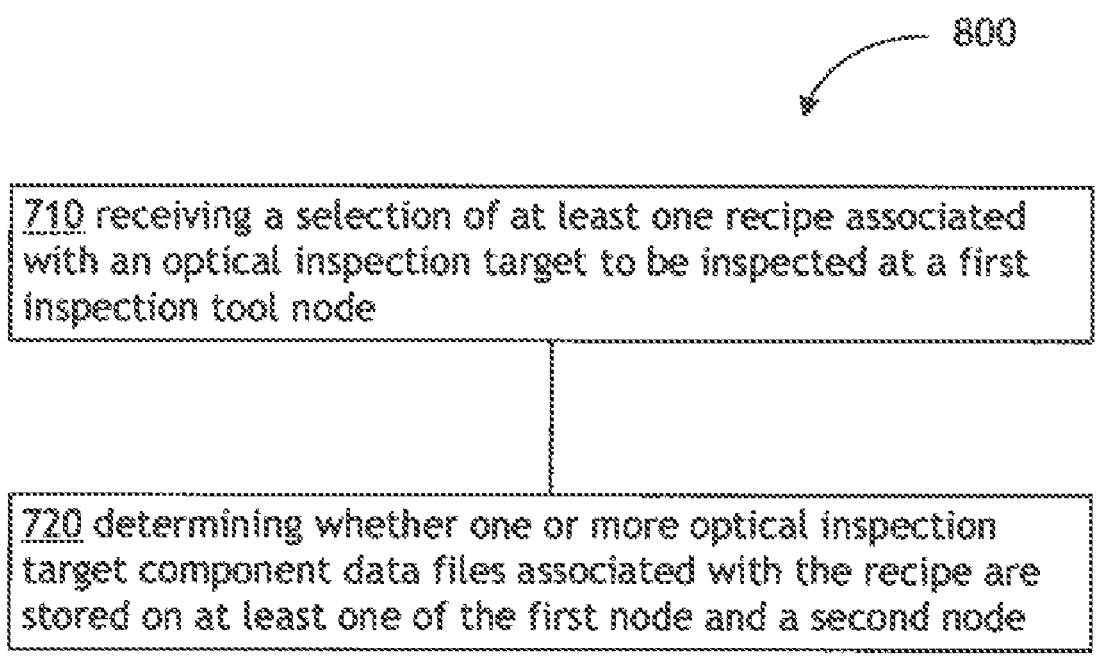
FIG. 7 shows a process for external recipe component distribution.

Referring to FIG. 7, a method 700 for optical inspection target component recipe distribution is illustrated. Operation 710 depicts receiving a selection of at least one recipe associated with an optical inspection target to be inspected at a first inspection tool node. For example, as shown in FIGS. 1-3, a user or automated agent (e.g. an inspection processing scheduling system) may determine that a particular optical inspection target is to be inspected. An input may be provided to an inspection tool node (e.g. a user input via a interface 104 of an inspection tool node 101A) referencing the desired optical inspection target. Initially, an optical inspection tool may attempt to fetch a recipe and the ERCs associated with the recipe's proxy component from its local cache and initiate inspection operations. However, it may be the case that a requested recipe and/or one of its ERC components is not present in the cache. In such a case, the inspection tool node 101A may query the RDS server 105 indicating that the inspection tool node 101A requires use of the recipe (e.g. $Recipe_{1.1}$).

Operation 720 depicts determining whether one or more external recipe components associated with the recipe are stored on at least one of the first inspection tool node and a second node. For example, as shown in FIGS. 1-3, when an inspection tool determines that it does not possess a requested recipe and has queried the RDS server 105, the RDS server 105 may access its RDS datastore 106 for the requested recipe (e.g. $Recipe_{1.1}$). The recipe (e.g. $Recipe_{1.1}$) may utilize one or more ERCs (e.g. $ERC_{1.1}$ residing in ERC datastore 103 of inspection tool node 101A and $ERC_{3.0}$ residing in ERC datastore 103 of inspection tool node 101B). Before returning the recipe, the RDS server 105 may determine if the ERCs of the recipe are local to the requesting inspection tool node (e.g. inspection tool node 101A) or are stored on a remote inspection tool node (e.g. inspection tool node 101B). If all required ERCs of the subject recipe are determined to be present at the requesting inspection tool node, the RDS server 105 may transmit the recipe to the inspection tool node 101A for further processing. If one or more ERCs are determined to reside on a remote inspection tool node, the RDS server 105 may initiate ERC fetch operations or return a "recipe get" error code to the requesting inspection tool node depending on system configuration.

Figure 8:
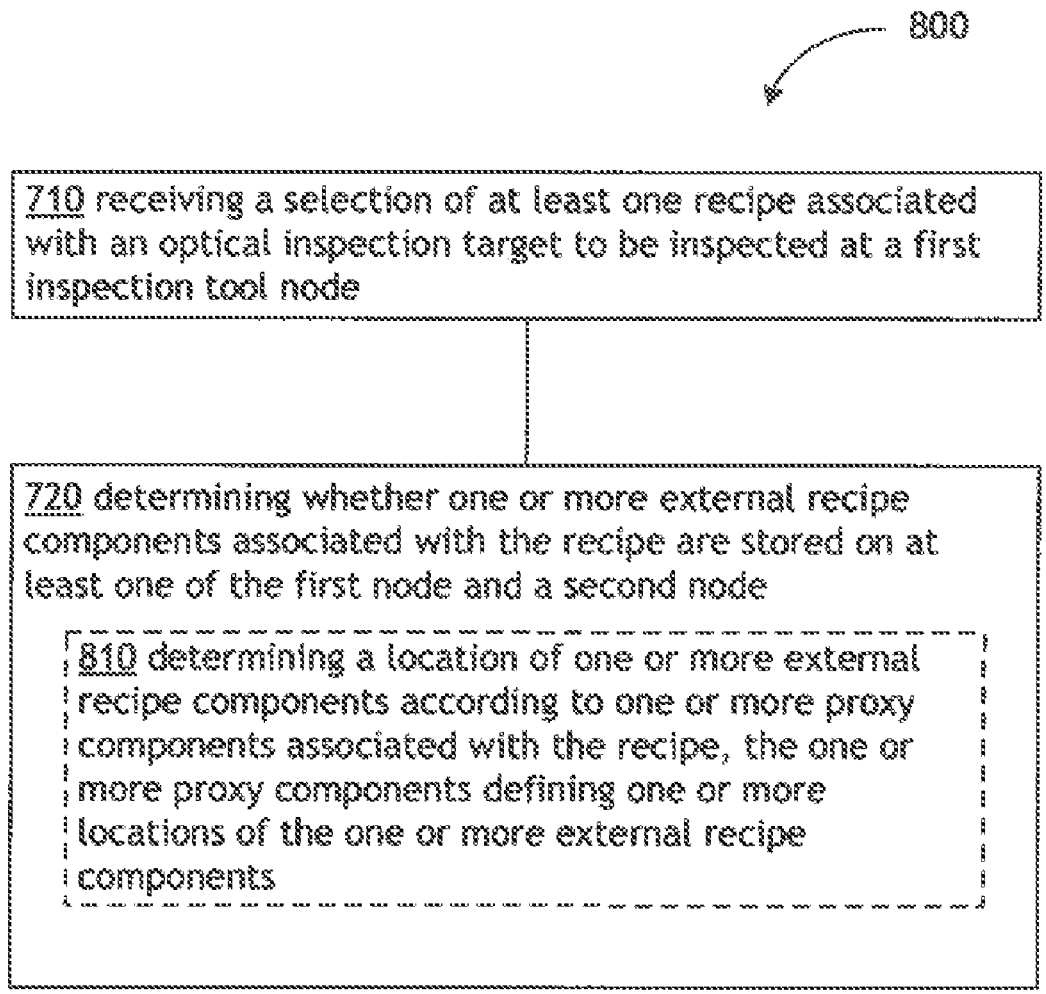
FIG. 8 shows a process for external recipe component distribution.

Referring to FIG. 8, the method 700 of FIG. 7 may include one or more additional operations. The operation 720 may include an operation 810.

Operation 810 depicts determining a location of one or more external recipe components according to one or more proxy components defining one or more locations of the one or more external recipe components. For example, as shown in FIGS. 1-3, upon receipt of a query regarding a recipe (e.g. $Recipe_{1.1}$) from an inspection tool node 101A, in order to determine whether a particular ERC is located on a requesting inspection tool node the RDS server 105 may retrieve proxy component (e.g. $Proxy_{1.1}$ and $Proxy_{3.0}$) associated with the recipe. The RDS server 105 may determine the locations of ERCs referenced by the proxy component of the recipe in order ascertain whether all of the necessary ERCs are present at the inspection tool node 101A or whether certain required ERCs are stored on remote inspection tool nodes 101 (e.g. inspection tool node 101B).

Figure 9:
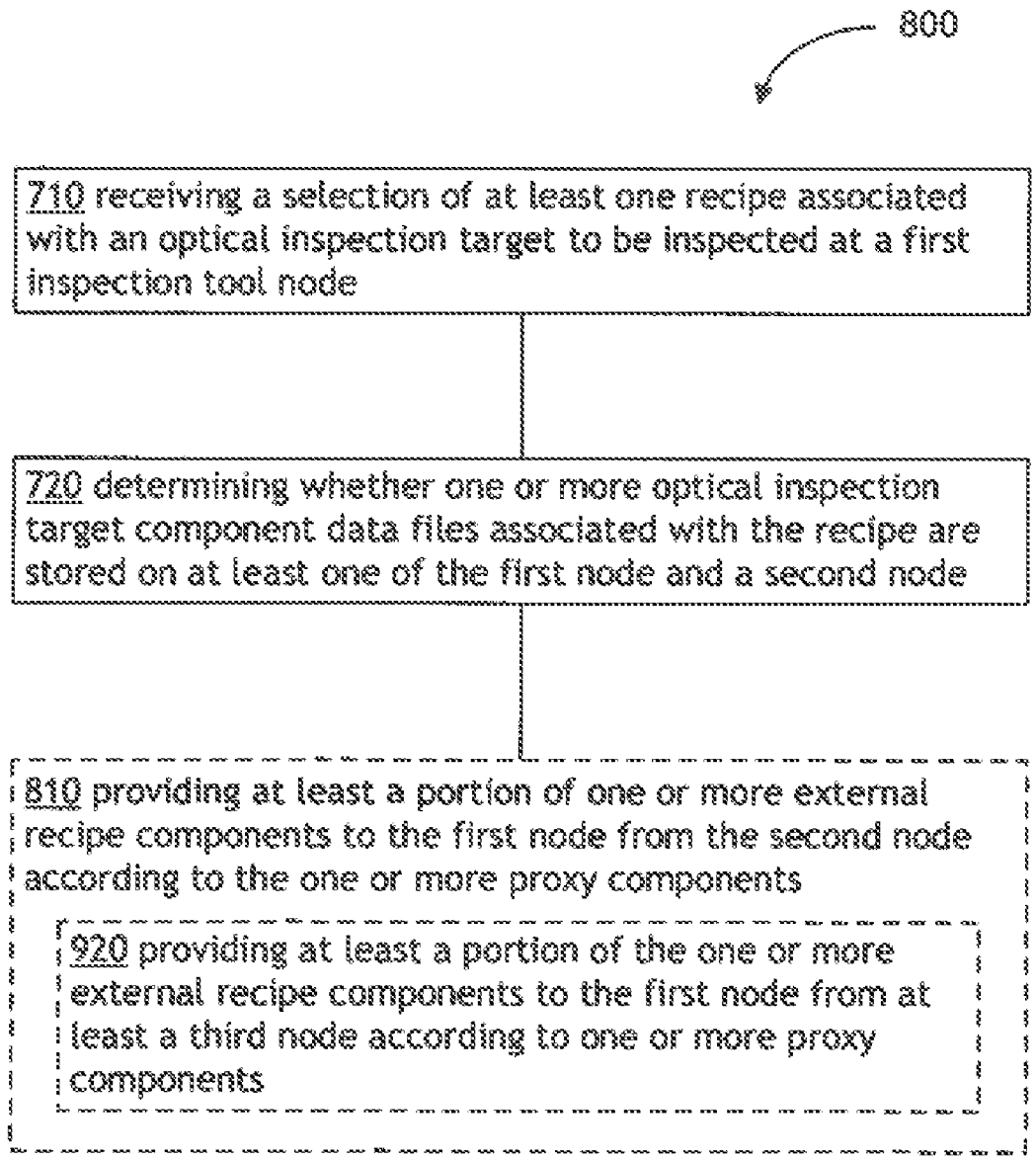
FIG. 9 shows a process for external recipe component distribution.

As described above, if one or more ERCs are determined to reside on a inspection tool node remote to a requesting inspection tool node, the RDS server 105 may initiate ERC fetch operations in order to provide the required ERC. Referring to FIG. 9, the method 700 of FIG. 7 may include one or more additional operations. The method 700 may include an operation 910, and/or an operation 920.

Operation 910 depicts providing at least a portion of one or more external recipe components to the first inspection tool node from the second node according to the one or more proxy components. For example, as shown in FIGS. 1-3, should an ERC for a particular recipe be determined to reside on a remote inspection tool node (e.g. inspection tool node 101B) as determined from the proxy component of recipe, the RDS server 105 may initiate a transfer of that ERC to the inspection tool node requesting the recipe. For example, the processing unit 110 of the RDS server 105 may query a source inspection tool node 101B to confirm that the requested ERC may be found in its ERC datastore 103. The RDS server 105 may query the destination inspection tool node 101A to confirm that sufficient storage space is available in its ERC datastore 103. The RDS server 105 may transmit a command to at least one of the inspection tool node 101A (e.g. as in a "pull" model) and the inspection tool node 101B (e.g. as in a "push" model) to initiate transfer of the ERC. The ERC may be transmitted via a network 111 connecting multiple inspection tool nodes 101. An inspection tool node 101 may provide an interface allowing a user to manually schedule an ERC distribution. The RDS server 105 may allow a user to specify a list of ERCs to be distributed to one or more target inspection tool nodes 101. The user may be able to monitor the progress of the system-wide ERC distributions at any point in time via a web interface 112.

Further, multiple inspection tool nodes 101 may be used for parallel transfer of respective portions of the ERC to a requesting inspection tool node. Operation 920 depicts providing at least a portion of the one or more external recipe components to the first inspection tool node from at least a third node according to one or more proxy components. For example, as shown in FIGS. 1-3, it may be the case that multiple inspection tool nodes 101 have copies of a particular version of an ERC (e.g. inspection tool node 101B and inspection tool node 101C may both maintain copies of $ERC_{3.0}$). In this case, the RDS server 105 may send a command to both the inspection tool node 101B and the inspection tool node 101C to each transfer a portion of an ERC corresponding to a recipe used by inspection tool node 101A (e.g. $ERC_{3.0}$ used in $Recipe_{1.1}$). The parallel transfer of respective portions of the ERC may serve to reduce the time required for a requesting inspection tool node to obtain requested ERCs.

The parallel transfer may be initiated at any time according to the availability of the various inspection tool nodes 101. For example, if a transfer of an ERC from a first source inspection tool node is in progress and a second source inspection tool node containing the ERC becomes available, the RDS server 105 may determine which portions of the ERC have not yet been provided to a destination inspection tool node and the RDS server 105 may initiate transfer of those portions from the second inspection tool node.

Figure 10:
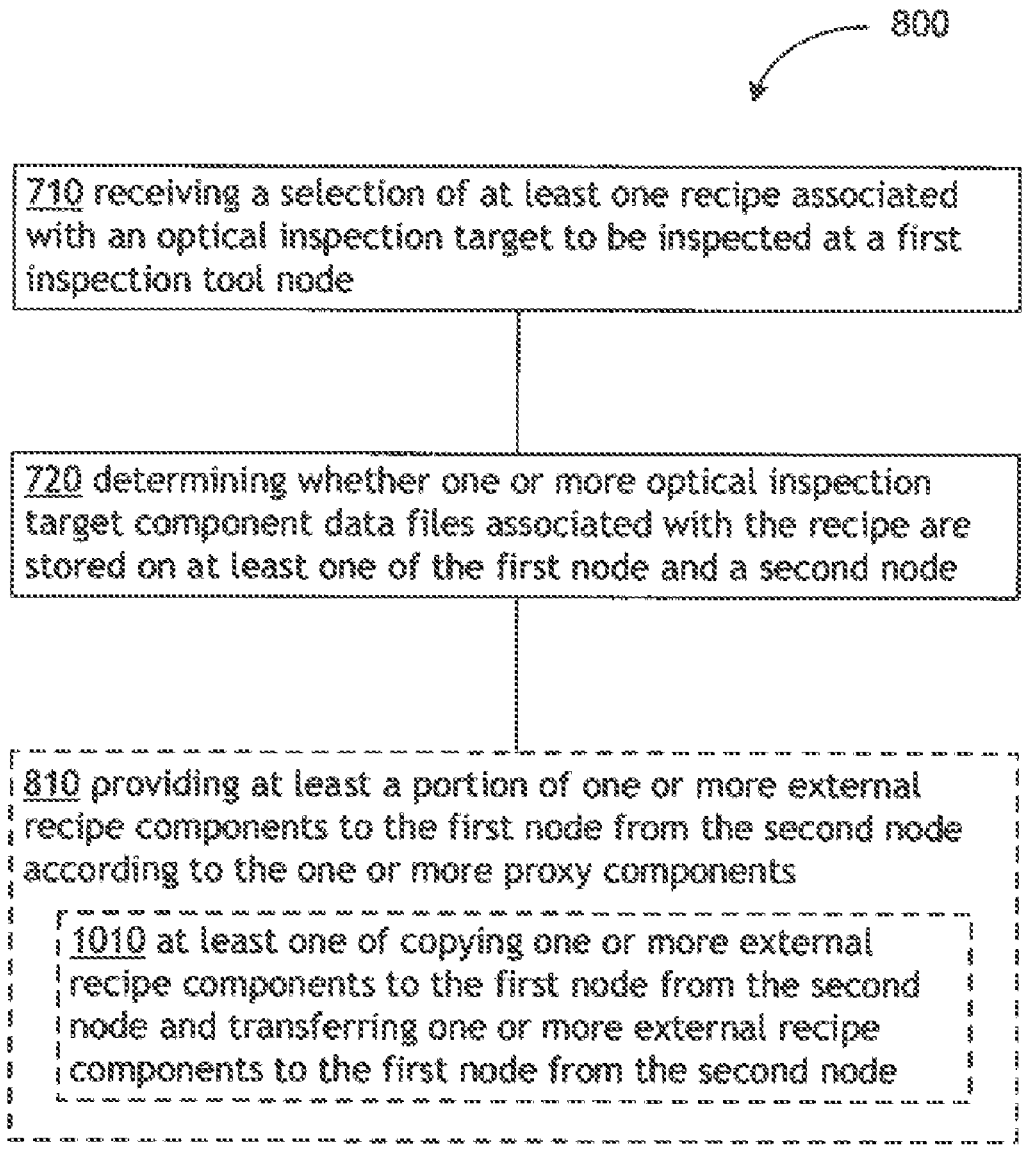
FIG. 10 shows a process for external recipe component distribution.

As described above, if one or more ERCs are determined to reside on a inspection tool node remote to a requesting inspection tool node, the RDS server 105 may initiate ERC fetch operations in order to provide the required ERC. Referring to FIG. 10, the method 700 of FIG. 9 may include one or more additional operations. The operation 910 may include an operation 1010.

Operation 1010 depicts at least one of copying one or more external recipe components to the first inspection tool node from the second node and transferring one or more external recipe components to the first inspection tool node from the second node. For example, as shown in FIGS. 1-3, in response to a command from the RDS server 105, the inspection tool node 101B may provide $ERC_{3.0}$ associated with $Recipe_{1.1}$ to inspection tool node 101A. In one instance, the $ERC_{3.0}$ may be copied to the ERC datastore 103 of inspection tool node 101A and a copy of $ERC_{3.0}$ may be retained on the ERC datastore 103 of inspection tool node 101B. In another instance, the $ERC_{3.0}$ may be copied to the ERC datastore 103 of inspection tool node 101A and a copy of $ERC_{3.0}$ may be deleted from the ERC datastore 103 of inspection tool node 101B. A determination of whether an ERC is copied or transferred between inspection tool nodes 101 may be made by the RDS server 105 based on ERC usage data maintained by the RDS server 105. For example, if a particular ERC maintained at an inspection tool node is not currently associated with any recipes stored at that inspection tool node that ERC may be transferred to a requesting inspection tool node and the ERC deleted from the local inspection tool node. Alternately, if an ERC maintained at an inspection tool node is associated with a recipe stored at the inspection tool node, the ERC may be copied to a requesting inspection tool and a copy of the ERC may be maintained at the local inspection tool node.

While the above descriptions have been provided with respect to the distribution and management of optical inspection recipes, it will be recognized that such systems and operations may be applied to any number of data processing activities associated with optical inspection. For example, following a particular inspection run, an inspection tool node may generate data regarding the inspection. Similar to the ERCs describe above, these lot results may be retained on the inspection tool node that generated them. The lot result data may be associated with a proxy component in the same manner as the ERCs. These proxy components may include a lot identifier, recipe identifier, time stamp, and the like. The use of an proxy component associated with the lot results facilitates the identification and location of the lot result data so that it may be routed to other inspection tool nodes by the RDS server 105 for analysis.

The foregoing detailed description has set forth various embodiments of the devices and/or processes via the use of block diagrams, flowcharts and/or examples. Insofar as such block diagrams, flowcharts and/or examples contain one or more functions and/or operations, it will be understood by those within the art that each function and/or operation within such block diagrams, flowcharts or examples can be implemented, individually and/or collectively, by a wide range of hardware, software, firmware or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise. While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

Although specific dependencies have been identified in the claims, it is to be noted that all possible combinations of the features of the claims are envisaged in the present application, and therefore the claims are to be interpreted to include all possible multiple dependencies. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for managing distributed external recipe components comprising:
    storing at least one external recipe component at an inspection tool node;
    associating at least one proxy component with the at least one external recipe component;
    associating the at least one external recipe component with at least one optical inspection target recipe; and
    storing the at least one optical inspection target recipe including the at least one proxy component in a recipe distribution server.

2. The method of claim 1, further comprising:
    modifying at least one external recipe components.

3. The method of claim 2, further comprising:
    updating at least one proxy components associated with at least one modified external recipe components.

4. The method of claim 1, further comprising:
    reallocating storage space on at least one inspection tool node.

5. The method of claim 4, wherein the reallocating storage space on at least one inspection tool node comprises:
    at least one of archiving and deleting at least one external recipe component.

6. The method of claim 4, wherein the reallocating storage space on at least one inspection tool node comprises:
    at least one of archiving and deleting at least one optical inspection target recipe.

7. The method of claim 4, further comprising:
restoring at least one of an archived external recipe component and an archived optical inspection target recipe to the inspection tool node.

8. A method for external recipe component distribution comprising:
receiving a selection of at least one recipe associated with an optical inspection target to be inspected at a first inspection tool node; and
determining whether one or more external recipe components associated with the recipe are stored on at least one of the first inspection tool node and a second inspection tool node.

9. The method of claim 8, wherein the step of determining whether one or more external recipe components associated with the recipe are stored on at least one of the first inspection tool node and the second inspection tool node comprises:
determining whether one or more external recipe components associated with the recipe are stored on at least one of the first inspection tool node and a the second inspection tool node according to one or more proxy components defining one or more locations of the one or more external recipe components.

10. The method of claim 9, further comprising:
providing at least a portion of one or more external recipe components to the first inspection tool node from the second inspection tool node according to the one or more proxy components.

11. The method of claim 10, wherein the step of providing at least a portion of one or more external recipe components to the first inspection tool node from the second inspection tool node according to the one or more proxy components comprises:
at least one of copying one or more external recipe components to the first inspection tool node from the second inspection tool node and transferring one or more external recipe components to the first inspection tool node from the second inspection tool node.

12. The method of claim 10, wherein the step of providing at least a portion of one or more external recipe components to the first inspection tool node from the second inspection tool node according to the one or more proxy components comprises:
providing one or more external recipe components to the first inspection tool node from the second inspection tool node according to an authorization.

13. A system for external recipe component distribution comprising:
a first optical inspection node including a datastore maintaining a first external recipe component;
a second optical inspection node including a datastore maintaining a second external recipe component;
a recipe distribution server including a datastore maintaining at least one optical inspection target recipe associated with the first external recipe component and the second external recipe component.

14. The system of claim 13, wherein the recipe distribution server is configured to:
receive a request from the first optical inspection node carry out an inspection of an optical inspection target employing the optical inspection recipe target; and
initiate the transfer of the second external recipe component from the second optical inspection node to the first optical inspection node.

15. The system of claim 14, wherein the recipe distribution server is configured to:
initiate the transfer of the second external recipe component from the second optical inspection node to the first optical inspection node according to the proxy component associated the second external recipe component.

16. The system of claim 13, wherein the at least one optical inspection target recipe comprises:
at least one proxy component associated with at least one of the first external recipe component and the second external recipe component.

* * * * *